United States Patent [19]

Marttila et al.

[11] Patent Number: 5,919,482
[45] Date of Patent: Jul. 6, 1999

[54] GELATINE CAPSULE CONTAINING SELEGILINE OR DERIVATIVE AND PARAFFIN AS CARRIER

[75] Inventors: Esko Veikko Marttila, Perttula; Ulla Inkeri Leinonen; Gunilla Margareta Örn, both of Turku, all of Finland

[73] Assignee: Orion-Yhtyma Oy, Espoo, Finland

[21] Appl. No.: 08/836,540

[22] PCT Filed: Dec. 15, 1995

[86] PCT No.: PCT/FI95/00683

§ 371 Date: Jun. 12, 1997

§ 102(e) Date: Jun. 12, 1997

[87] PCT Pub. No.: WO96/19981

PCT Pub. Date: Jul. 4, 1996

[30] Foreign Application Priority Data

Dec. 23, 1994 [GB] United Kingdom ............... 9426079

[51] Int. Cl.$^6$ ...................................................... A61K 9/48
[52] U.S. Cl. .................. 424/456; 424/451; 424/452; 424/455; 514/789
[58] Field of Search ................................. 424/451, 452, 424/455, 456; 514/789

[56] References Cited

U.S. PATENT DOCUMENTS 4,812,481   3/1989   Reischig et al. .................. 514/647

FOREIGN PATENT DOCUMENTS

| 146363 | 6/1985 | European Pat. Off. |
| 451484 | 10/1991 | European Pat. Off. |
| 467164 | 1/1992 | European Pat. Off. |
| 2290965 | 1/1996 | United Kingdom |
| 94/22435 | 10/1994 | WIPO |

OTHER PUBLICATIONS

J. P. Stanley, Soft Gelatin Capsules, *The Theory and Practice of Industrial Pharmacy*, Ed. Lachman et al., Third Edition, Lea & Febiger, 1986, 398–412.

P.A. Veronesi, "Unit Dosage Delivery System for Hydrophobic Drugs", AN 96–051911, Database WPI, Week 9606, Jan. 1996, Derwent Publications Ltd., London, GB.

*Primary Examiner*—Thurman K. Page
*Assistant Examiner*—James M. Spear
*Attorney, Agent, or Firm*—Finnegan, Henderson, Farabow, Garrett & Dunner, L.L.P.

[57] ABSTRACT

The invention relates to a gelatine capsule containing selegiline, its structurally related compounds or their pharmaceutically acceptable salts as the active ingredient and paraffin as a carrier. Preferably, the gelatin capsule is a soft gelatine capsule, and paraffin is substantially in liquid form.

11 Claims, No Drawings

GELATINE CAPSULE CONTAINING SELEGILINE OR DERIVATIVE AND PARAFFIN AS CARRIER

This application is a 371 of PCT/FI95/00683 filed Dec. 15, 1995.

The invention relates to a gelatine capsule containing selegiline, or a structurally related compound or pharmaceutically acceptable salt thereof and paraffin as a carrier.

Selegiline ((-)N-(1-phenyl isopropyl)-N-methyl-N-propionyl amine) is a MAO-B inhibitor. It has been available in tablet form for more than ten years in the treatment of Parkinson's disease and for a few years as an aqueous mixture.

Gelatine capsules provide an alternative to the present compositions of selegiline worthy of consideration because the pharmaceutical availability of drugs formulated for this kind of dosage form may be regulated more efficiently. Furthermore, the accuracy and uniformity of dosage are usually better in formulations having liquid contents than in entirely dry formulations.

Different problems to those connected with the preparation of conventional solid oral formulations are encountered when a gelatine capsule, especially a soft gelatine capsule, of a new drug is prepared. In soft gelatine capsules, the active drug is usually dissolved or suspended in a suitable liquid, e.g. vegetable oil. Hard gelatine capsules are usually prepared using principally the same technology as in conventional solid oral formulations (i.e. tablets, granules etc.). However, it is also possible to prepare hard gelatine capsules having liquid or semi-solid contents. If liquid contents are to be used in hard gelatine capsules then a special sealing technology of the capsules is needed.

According to U.S. Pat. No. 4,812,481 selegiline and amantadine act together synergistically in the treatment of Parkinsonism. The active ingredients may be administered either sequentially or in a single formulation. Numerous formulation agents are mentioned and several types of preparation are mentioned. The examples illustrate a suspension of amantadine hydrochloride and selegiline in water for injection, and capsules of amantadine hydrochloride and selegiline hydrochloride granulated with gelatin, corn starch, magnesium stearate and silicon dioxide, which mixture is used to fill hard gelatin capsules.

When the stability of selegiline hydrochloride was tested in vegetable oil suspensions which are typically used in gelatine capsules having liquid contents the active ingredient was degraded within a few weeks. However, in liquid paraffin suspension no degradation of selegiline hydrochloride was detected even after a storage period of 11 weeks at 45° C.

It is therefore the object of the invention to provide a gelatine capsule of selegiline, a structurally related compound or pharmaceutically acceptable salt thereof.

It is a further object of the invention to provide the use of a paraffin carrier, especially a paraffin oil carrier, in gelatine capsules of selegiline, a structurally related compound or pharmaceutically acceptable salt thereof.

It is a still further object of the invention to provide a liquid carrier which may be used in gelatine capsules of selegiline, a structurally related compound or pharmaceutically acceptable salt thereof.

By the definition "structurally related compound" it is meant that especially the side chain of the compound is structurally similar to that of selegiline i.e. said compound is isopropylpropynylamine derivative.

The gelatine capsules according to the invention may be prepared using conventional techniques (see eg. The Theory and Practice of Industrial Pharmacy, Ed. Lachman L. et al, Third Edition, Lea & Febiger, 1986, Philadelphia, pp. 398–412). The amount of selegiline, a structurally related compound or pharmaceutically acceptable salt thereof, may be about from 2.5 to 60 mg per unit dosage, the amount of paraffin being from 2 to 250, preferably from about 5 to about 50 parts by weight relative to 1 part by weight of selegiline. A substantial part of paraffin, i.e. preferably at least 50% by weight and (especially in soft gelatine capsules) most preferably at least 80% by weight, is added in liquid form (paraffin oil). However, especially in hard gelatine capsules up to 85 weight % solid paraffin may also be used.

In addition to paraffin the carrier may also contain small amounts of other typical liquid carriers used in soft gelatine capsules such as a vegetable oil, especially arachidis oil or sesame oil. However, paraffin oil should be the major liquid carrier.

The contents of the gelatine capsules may further include other active ingredients such as dopaminergic agonists or levodopa, suspending agents and pharmaceutically acceptable acids which are compatible with selegiline hydrochloride. Unit dosages needed for other suitable active ingredients have been desribed e.g. in U.S. Pat. No. 4,812,481 (amantadine), EP-B1-146363 (phenylalanine), EP-A1-451 484 (levodopa and a peripheral decarboxylase 5 inhibitor) and EP-A2-467164 (flurpitin). Suitable acids have been disclosed in the PCT patent application WO 94/22435.

COMPARISON TESTS

The results of tests comparing the stability of selegiline hydrochloride in paraffin oil, arachidis oil, sesame oil, olive oil, soybean oil and amygdale oil are presented in Table 1. The tests were carried out by storing selegiline hydrochloride in the liquid to be tested (0.5 g/9.5 g) for four weeks at 45° C. The degraration was followed by TLC.

TABLE 1

The degradation of selegiline hydrochloride in different media

| Medium | Results |
|---|---|
| Arachidis oil | 6 impurity spots, all < 0.1% |
| Sesame oil | 6 impurity spots, all < 0.1% |
| Olive oil | 8 impurity spots, 1 < 0.5%, 2 = 0.1%, 5 < 0.1% |
| Soybean oil | 8 impurity spots, 1 = 0.2%, 2 = 0.1%, 5 < 1% |
| Amygdale oil | 8 impurity spots, 1 < 0.5%, 1 < 0.2%, 6 < 0.1% |
| Paraffin liq. | 1 impurity spot < 0.1% |

The following examples describe how the gelatine capsules according to the invention may be prepared.

EXAMPLE 1

| | |
|---|---|
| Selegiline hydrochloride | 2.5 mg |
| Liquid paraffin | 100.0 mg |

Selegiline hydrochloride is sieved and suspended in liquid paraffin to form a homogenous suspension. The suspension is used to fill soft gelatine capsules.

EXAMPLE 2

| Selegiline hydrochloride | 10.0 mg |
|---|---|
| Liquid paraffin | 160.0 mg |
| Solid paraffin | 40.0 mg |

Selegiline hydrochloride is sieved. Solid paraffin is melted, liquid paraffin is mixed into the melt and selegiline hydrochloride is suspended in the liquid to form a homogenous suspension. The suspension is used to fill soft gelatine capsules.

EXAMPLE 3

| Selegiline hydrochloride | 5.0 mg |
|---|---|
| Liquid paraffin | 150.0 mg |
| Solid paraffin | 50.0 mg |

Selegiline hydrochloride is sieved. Solid paraffin is melted, liquid paraffin is mixed into the melt and selegiline hydrochloride is suspended in the liquid to form a homogenous suspension. The mixture is used to fill hard gelatine capsules.

We claim:

1. A gelatine capsule comprising a compound, wherein said compound is selegiline or a pharmaceutically acceptable salt thereof, and paraffin as a carrier, wherein the amount of paraffin is from 2 to 250 parts by weight relative to 1 part by weight of said compound, and wherein at least 15% by weight of paraffin is in liquid form.

2. The capsule of claim 1, wherein the amount of paraffin is from 5 to 50 parts by weight relative to 1 part by weight of said compound.

3. The capsule of claim 1, wherein the amount of said compound is from about 2.5 to 60 mg per unit dose.

4. The capsule of any of claims 1–3, wherein the capsule is a soft gelatine capsule.

5. The capsule of claim 4, wherein at least 80% by weight of paraffin is in liquid form.

6. The capsule of claim 4, wherein at least 50% by weight of paraffin is in liquid form.

7. A process for preparing a gelatine capsule comprising a compound, wherein said compound is selegiline or a pharmaceutically acceptable salt thereof, wherein said process comprises preparing a suspension of said compound and paraffin and filling said capsule with said suspension, wherein the amount of paraffin is from 2 to 250 parts by weight relative to 1 part by weight of said compound, and wherein at least 15% by weight of paraffin is in liquid form.

8. The process of claim 7, wherein the amount of paraffin is from 5 to 50 parts by weight relative to 1 part by weight of said compound.

9. The process of claim 7 or 8, wherein the capsule is a soft gelatine capsule.

10. The process of claim 9, wherein at least 50% by weight of paraffin is in liquid form.

11. The process of claim 9, wherein at least 80% by weight of paraffin is in liquid form.

* * * * *